US00PP34219P2

(12) United States Plant Patent
Grazzini

(10) Patent No.: US PP34,219 P2
(45) Date of Patent: May 10, 2022

(54) ***LAGERSTROEMIA* PLANT NAMED 'G19234'**

(50) Latin Name: *Lagerstroemia indica*
Varietal Denomination: G19234

(71) Applicant: Garden Genetics, Bellefonte, PA (US)

(72) Inventor: Richard A. Grazzini, Bellefonte, PA (US)

(73) Assignee: Garden Genetics llc, Bellefonte, PA (US)

( * ) Notice: Subject to any disclaimer, the term of this patent is extended or adjusted under 35 U.S.C. 154(b) by 0 days.

(21) Appl. No.: 17/354,146

(22) Filed: Jun. 22, 2021

(51) Int. Cl.
*A01H 6/00* (2018.01)
*A01H 5/02* (2018.01)

(52) U.S. Cl.
USPC ..... Plt./252

(58) Field of Classification Search
USPC ..... Plt./252
CPC ..... A01H 6/00; A01H 5/02
See application file for complete search history.

*Primary Examiner* — Keith O. Robinson
(74) *Attorney, Agent, or Firm* — Cassandra Bright

(57) ABSTRACT

A new and distinct cultivar of *Lagerstroemia* plant named 'G19234' is disclosed, characterized by bright magenta-rose colored flowers. Plants have a compact, mounded habit with dense branching. The new variety has a long blooming period and shows strong field resistance to powdery mildew. Inflorescences are held outside of the plant canopy, creating an umbrella-like floral display. The new variety is a *Lagerstroemia*, normally used for outdoor ornamental purposes.

2 Drawing Sheets

Figure 1:
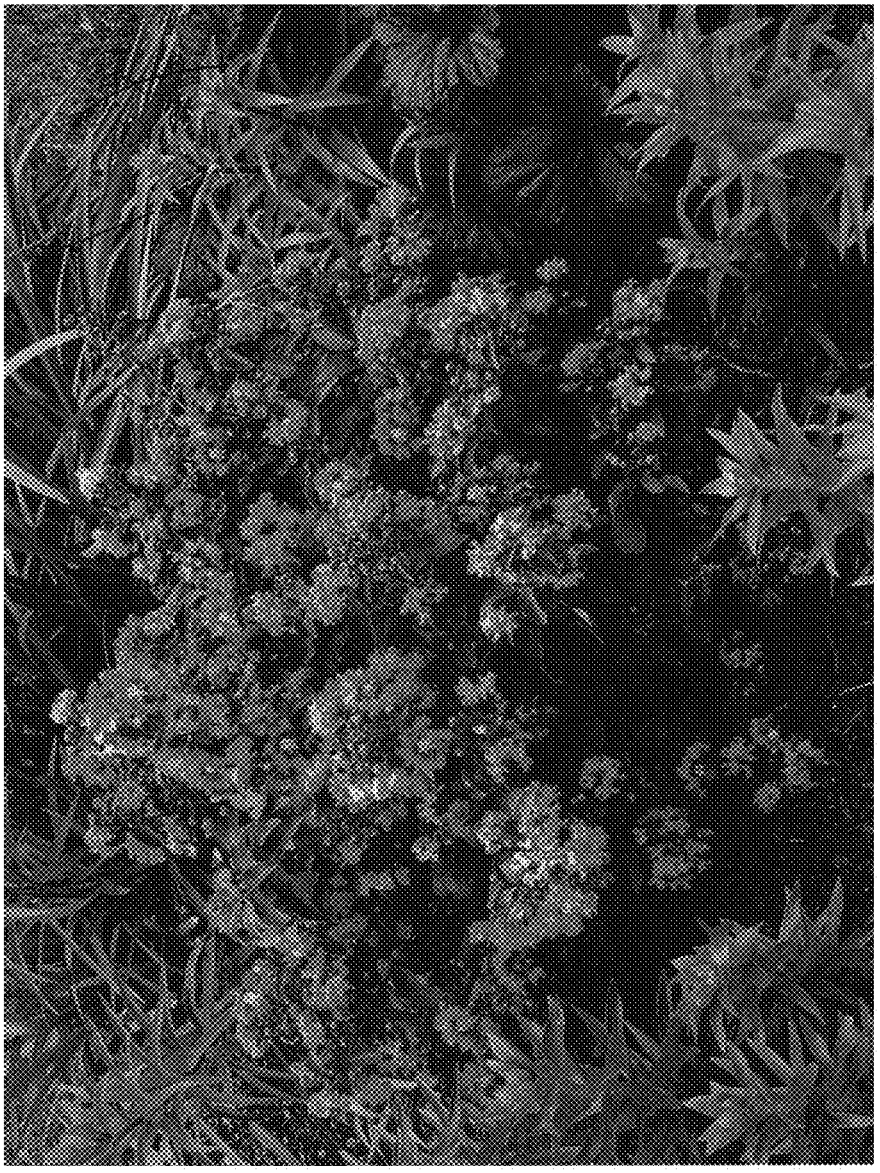

Latin name of the genus and species: *Lagerstroemia indica.*

Variety denomination: 'G19234'.

BACKGROUND OF THE INVENTION

The new *Lagerstroemia* cultivar is a product of a planned breeding program conducted by the inventor at a research nursery in Bellefonte, Pa. The objective of the breeding program was to develop new Crepe Myrtle plants with compact habits for ornamental uses. The open-pollination resulting in this new variety was made during September of 2017.

The seed parent is the unpatented proprietary variety referred to as *Lagerstroemia* '13325-1'. The pollen parent cannot be exactly identified. The new variety was selected in July of 2018 by the inventor in a group of seedlings resulting from the 2017 cross-pollination, in a nursery in Bellefonte, Pa.

Asexual reproduction of the new cultivar was performed by softwood cuttings. This was first performed at the same nursery in Bellefonte, Pa. during August of 2018, and has shown that the unique features of this cultivar are stable and reproduced true to type in multiple successive generations.

SUMMARY OF THE INVENTION

The cultivar 'G19234' has not been observed under all possible environmental conditions. The phenotype may vary somewhat with variations in environment such as temperature, day length, and light intensity, without, however, any variance in genotype.

The following traits have been repeatedly observed and are determined to be the unique characteristics of 'G19234'. These characteristics in combination distinguish 'G19234' as a new and distinct *Lagerstroemia* cultivar:

1. Compact, mounded habit
2. Strong field tolerance to powdery mildew
3. Bright magenta-rose flower color
4. Dense branching
5. Floral display on the outside of the canopy, creating an umbrella-like display
6. Long blooming period

PARENT COMPARISON

Plants of the new cultivar 'G19234' are similar to plants of the seed parent in most horticultural characteristics; however, plants of the new cultivar 'G19234' differ in the following:

1. 'G19234' is dwarf and compact; seed parent '13325-1' is less dwarf and more open in habit.
2. 'G19234' has mid-green foliage. Seed parent '13325-1' has darker grey-green foliage.
3. 'G19234' has bright rose-magenta colored flowers. Seed parent '13325-1' has softer rose colored flowers.
4. Flowers of new variety 'G19234' are on the outside of the canopy, forming an umbrella-like display. Flowers of the seed parent '13325-1' are on the tips of their branches, creating a looser, less full display.
5. 'G19234' exhibits a much stronger field tolerance to powdery mildew when compared to seed parent 13325-1.

The pollen parent cannot be exactly identified.

COMMERCIAL COMPARISON

Plants of the new cultivar 'G19234' are comparable to the commercial variety *Lagerstroemia* 'G2X133271', U.S. Plant Pat. No. 27,474. The two *Lagerstroemia* varieties are similar in most horticultural characteristics, however, the new variety 'G19234' differs in the following;

1. New variety 'G19234' is dwarf, mounded and compact. Comparison variety 'G2X133271' is less compact.

2. New variety 'G19234' has a distinctly mounded plant habit. Comparison variety 'G2X133271' is more open and upright.
3. The floral display of new variety 'G19234' covers its canopy in an umbrella-like manner. Comparison variety 'G2X133271' displays its numerous flowers in a looser, more open way.
4. New variety 'G19234' has mid-green colored foliage. Comparison variety 'G2X133271' has dark-green foliage.
5. New variety 'G19234' has bright rose-magenta colored flowers. Flowers of comparison variety 'G2X133271' are a lighter shade of rose-magenta.

Plants of the new cultivar 'G19234' are comparable to the commercial variety *Lagerstroemia* 'Cherry Mocha', U.S. Plant Pat. No. 28,281. The two *Lagerstroemia* varieties are similar in most horticultural characteristics; however, the new variety 'G19234' differs in the following;

1. New variety 'G19234' has dark-green foliage at leaf emergence. Comparison variety 'Cherry Mocha' has burgundy-colored leaves at emergence.;
2. New variety 'G19234' is dwarf and mounded in habit. Comparison variety 'Cherry Mocha' is taller and more upright.;
3. The flower color of new variety 'G19234' is a bright magenta-rose. Comparison variety 'Cherry Mocha' has darker cherry-red flowers.;
4. New variety 'G19234' has smaller leaves held in a flatter orientation than comparison variety 'Cherry Mocha' which has larger, more upright leaves.;
5. New variety 'G19234' is more densely branched than comparison variety 'Cherry Mocha'.

BRIEF DESCRIPTION OF THE PHOTOGRAPHS

The accompanying photograph in FIG. 1 illustrates a typical flowering plant of 'G19234' grown outdoors in Bellefonte, Pa. at approximately 6 months old.

Figure 2:
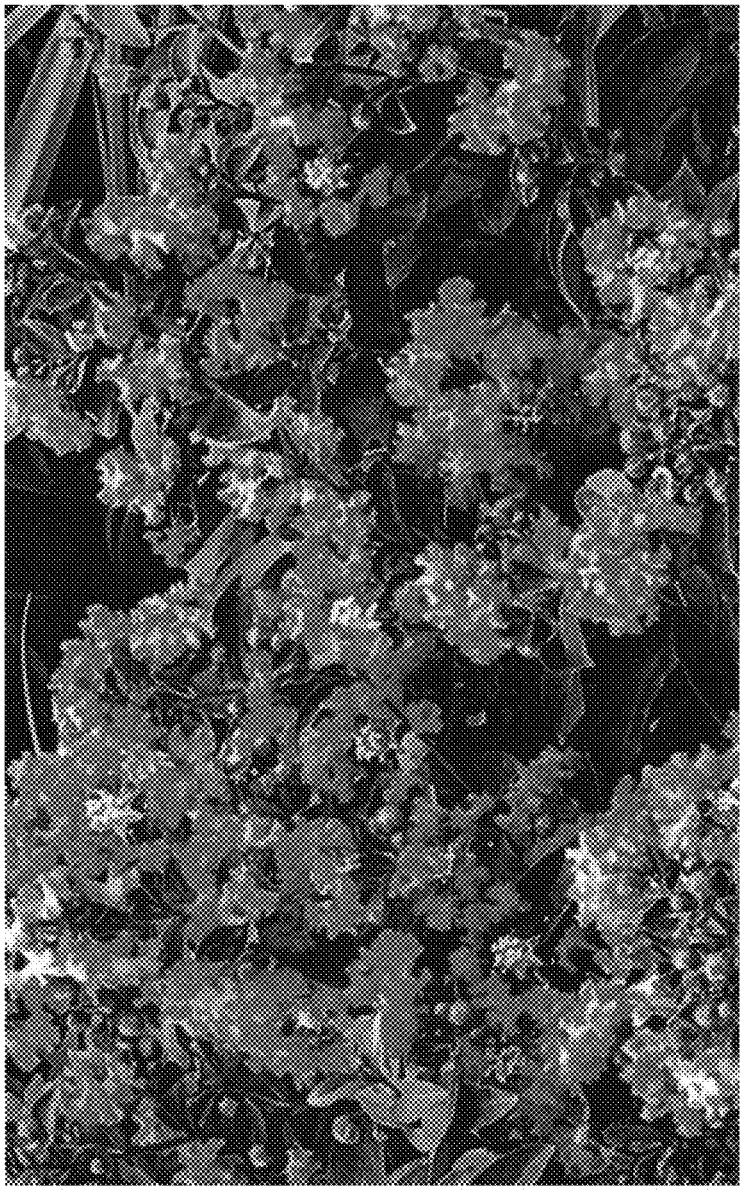

FIG. 2 illustrates a close-up of the inflorescences.

The photographs were taken using conventional techniques and although colors may appear different from actual colors due to light reflectance it is as accurate as possible by conventional photographic techniques.

DETAILED BOTANICAL DESCRIPTION

In the following description, color references are made to The Royal Horticultural Society Colour Chart 2015 except where general terms of ordinary dictionary significance are used. The following observations and measurements describe 'G19234' plants grown outdoors in Bellefonte, Pa. The growing temperature ranged from approximately 18° C. to 28° C. during the day and from approximately 6° C. to 12° C. during the night. General light conditions are normal sunlight and numerical values represent averages of typical plant types. Measurements were taken during August of 2019 and August of 2020.

Botanical classification: *Lagerstroemia indica* 'G19234'.

PROPAGATION

Type of propagation typically used: Softwood cuttings.
Time to initiate roots: 10 to 14 days at about 24° C.
Time to produce a rooted cutting: 21 to 28 days at about 24° C.
Root description: Thin fibrous, dense, moderate branching. White in color, not accurately measured with RHS Chart.

PLANT

Age of plant described: About 6 months old from a rooted cutting.
Container size: 3-liter container.
Overall plant shape: Mounded and upright.
Plant form: Flowering shrub.
Growth habit: Compact, dwarf.
Plant spread: 95-110 cm.
Plant height: 70-80 cm.
Growth rate: Rapid.
Plant vigor: Strong.
Branching habit: Dense, upright.
Length of primary lateral branches: 60 cm.
Diameter of lateral branches: 8-10 mm.
Quantity of lateral branches: About 40.
Stem:
- *Color.*—Young growth: Near RHS Greyed-Purple 183B.
- *Color.*—Old growth, between RHS Greyed-Purple 183B and Greyed-Orange 177A.
- *Shape.*—Round.
- *Strength.*—Strong.
- *Aspect angle.*—Mostly upright.
- *Texture.*—Smooth to slightly pubescent, then woody with age.

Internode length: About 3 cm.
Bark peel: Not observed.

FOLIAGE

Leaf:
- *Arrangement.*—Sub-opposite or opposite.
- *Average length.*—3.5 cm.
- *Average width.*—2.0 cm.
- *Shape of blade.*—Elliptical to ovate.
- *Apex.*—Acute.
- *Base.*—Obtuse to cordate.
- *Margin.*—Entire.
- *Texture of top surface.*—Smooth to slightly ribbed. Glabrous.
- *Texture of bottom surface.*—Smooth with prominent veins in a pinnate pattern.
- *Color.*—Young foliage upper side: Near RHS Yellow-Green 144B. Young foliage under side: Near RHS Yellow-Green 144C. Mature foliage upper side: Near RHS Green 137A. Mature foliage under side: Near RHS Green 138B. Venation: Type: Pinnate. Mature Venation color upper side: Near RHS Yellow-Green 153A. Mature Venation color under side: Near RHS Greyed-Green 195B. Immature Venation color upper side: Near RHS Greyed-Red 179B. Immature Venation color under side: Near RHS Greyed-Green 195B.
- *Petiole.*—Length: 1 mm. Diameter: 1 mm. Texture, upper side: Smooth. Texture, under side: Smooth. Color upper and lower surfaces: Near RHS Green 143A.

FLOWER

Natural flowering season: Late June until October.
Inflorescence form: Panicle.

Flowers per inflorescence: About 25 open flowers and 50 buds.

Inflorescence size:
*Width.*—20 cm.
*Height.*—Average 20 cm.

Individual flowers:
*Type.*—Rotate.
*Shape.*—Obovate.
*Habit.*—Whorled outward.
*Diameter.*—4.0 cm.
*Depth.*—2.0 cm.
*Persistence.*—Self-cleaning.
*Fragrance.*—Light floral scent.

Petals:
*Arrangement.*—Whorled.
*Number.*—6.
*Shape.*—Overall irregular orbicular.
*Aspect.*—Undulate.
*Margin.*—Undulate, loosely crenate.
*Tip shape.*—Rounded.
*Base shape.*—Rounded.
*Length.*—1.5 cm.
*Width.*—1.5 cm.
*Texture.*—Upper: Glabrous. Lower: Glabrous.
*Color.*—When opening: Upper surface: Near RHS Red-Purple 63A. Under surface: Near RHS Red-Purple 63A. Fully opened: Upper surface: Near RHS Red-Purple 63A. Under surface: Near RHS Red-Purple 63A and Red 58D.

Bud:
*Shape.*—Sphere.
*Length.*—7 mm.
*Diameter.*—8 mm.
*Color.*—Near RHS Yellow-Green 145B.
*Prominence of suture.*—Strong.

Calyx:
*Shape.*—Unguiculate.
*Length.*—11 mm.
*Diameter.*—5 to 10 mm.

Sepals:
*Appearance.*—Glossy.
*Arrangement.*—Rotate, fused.
*Shape.*—Narrowly triangular.
*Tip shape.*—Acute.
*Base shape.*—Obtuse.
*Margin.*—Entire.
*Quantity per flower.*—6.
*Length.*—9 mm.
*Width.*—3.5 mm.
*Margin.*—Entire.
*Texture.*—Inner: Coriaceous, rugose. Outer: Smooth.
*Color.*—Inner: Near RHS Yellow-Green 144B. Outer: Near RHS Yellow-Green 145C.

Peduncle:
*Length.*—Average 1.0 cm.
*Diameter.*—1 mm.
*Texture.*—Glabrous.
*Color.*—Near RHS Yellow-Green 145B.
*Orientation.*—Upright and outward.
*Strength.*—Strong.

Pedicel:
*Length.*—1.3 cm.
*Diameter.*—8 mm.
*Angle.*—Less than 45 degrees from attachment.
*Strength.*—Good.
*Texture.*—Smooth.
*Color.*—Near Yellow-Green 145B.

REPRODUCTIVE ORGANS

Stamens:
*Number.*—About 30.
*Filament length.*—1 cm.
*Filament color.*—Near Red-Purple 70D.

Anthers:
*Shape.*—Linear.
*Length.*—1 mm.
*Color.*—Greyed-Orange 163A.
*Pollen.*—Sparse, colored near Greyed-Orange 163A.

Pistil:
*Number.*—1.
*Length.*—1.5 cm.

Stigma:
*Shape.*—Globular.
*Color.*—Near RHS Greyed-Green 189A.
*Ovary color.*—Near RHS Yellow 11B.

OTHER CHARACTERISTICS

Fruits and seeds: Not observed to date.

Disease/pest resistance: Shows good field-tolerance to leaf spots and powdery mildew. The observed resistance to mildew is assumed to be for the pathogen *Erysiphe lagerstroemiae*. Typically leaf spot on *Lagerstroemia* is caused by *Cercospora lythracearum*.

Temperature range: Observed to tolerate a temperature range from about −25° C. to 35° C. Root hardy to −28° C., with plant dying back, but, surviving.

What is claimed is:

1. A new and distinct cultivar of *Lagerstroemia* plant named 'G19234' as herein illustrated and described.

* * * * *